US006512114B1

(12) United States Patent
Dhaon et al.

(10) Patent No.: US 6,512,114 B1
(45) Date of Patent: Jan. 28, 2003

(54) PROCESS FOR THE PREPARATION OF MIDAZOLAM

(75) Inventors: Madhup K. Dhaon, Mundelein, IL (US); Grant L. Esser, Des Plaines, IL (US); Deborah A. Davis, Gurnee, IL (US); Ashok V. Bhatia, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/344,280

(22) Filed: Jun. 30, 1999

(51) Int. Cl.$^7$ .............................. C07D 487/12
(52) U.S. Cl. ..................... 540/562
(58) Field of Search ........................... 540/562

(56) References Cited

U.S. PATENT DOCUMENTS

| 4,280,957 A | 7/1981 | Walser et al. ............. 260/244.4 |
| 4,377,523 A | 3/1983 | Walser et al. ............. 260/244.4 |
| 4,440,685 A | 4/1984 | Walser et al. ............. 260/245.6 |
| 5,693,795 A | * 12/1997 | Bender et al. .............. 540/562 |

FOREIGN PATENT DOCUMENTS

| EP | 0 768310 A1 | 4/1997 |
| GB | 1549836 | 8/1979 |

OTHER PUBLICATIONS

J. Pharmaceutical Sciences, 1977, 66:1–19.

* cited by examiner

Primary Examiner—Brenda Coleman

(74) Attorney, Agent, or Firm—B. Gregory Donner

(57) ABSTRACT

The present invention provides a process for the synthesis of Midazolam I

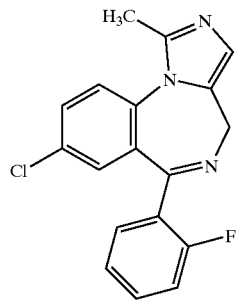

from a compound of formula II,

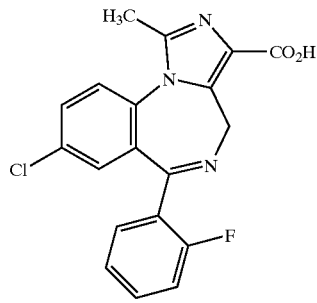

using thermodynamic, basic workup conditions. Additional steps to isolate the pure bulk product follow.

12 Claims, No Drawings

PROCESS FOR THE PREPARATION OF MIDAZOLAM

TECHNICAL FIELD

The present invention relates to a process for the preparation of 8-chloro-6-(2-fluorophenyl)-1-methyl-4H-imidazo[1,5-a][1,4]benzodiazepine (Midazolam) from 8-chloro-6-(2-fluorophenyl)-1-methyl-4H-imidazo[1,5-a][1,4]benzodiazepine-3-carboxylic acid (tricyclic acid).

BACKGROUND OF THE INVENTION 8-chloro-6-(2-fluorophenyl)-1-methyl-4H-imidazo[1,5-a][1,4]benzodiazopine (Midazolam), a pre-operative anesthetic, belongs to a class of imidazobenzodiazepine compounds which are useful as anticonvulsants, sedatives, and muscle relaxants.

The last step in the synthesis of Midazolam is thermal decarboxylation of 8-chloro-6-(2-fluorophenyl)-1-methyl-4H-imidazo[1,5-a][1,4]benzodiazopine-3-carboxylic acid (tricyclic acid). Also produced in this step is 8-chloro-6-(2-fluorophenyl)-1-methyl-6H-imidazo[1,5-a][1,4]benzodiazopine (Isomidazolam) and decomposition biproducts resulting from high temperature dehalogenation and dimerization of tricyclic acid. Removal of the decomposition biproducts and purification of Midazolam and Isomidazolam are accomplished by column chromatography (GB Patent 1,549,836 and U.S. Pat. Nos. 4,280,957, 4,440,685 and 4,377,523), a method which is impractical for large scale preparation of Midazolam because of the costly chromatography equipment required.

Attempts at improving the overall yield of Midazolam have focused on isomerizing purified Isomidazolam to Midazolam by treatment of the former with potassiun tert-butoxide in N,N-dimethylformamide (DMF) under kinetically controlled conditions (U.S. Pat. Nos. 4,377,523 and 4,440,685). This method is also impractical for large scale syntheses of Midazolam because of the amount of thermal energy required for removal of the DMF.

Thus, there is a continuing need in the pharmaceutical manufacturing industry for a large scale conversion of tricyclic acid to Midazolam which minimizes Isomidazolam formation and provides for non-chromatographic removal of biproducts.

SUMMARY OF THE INVENTION

The process of the present invention provides a large scale conversion of tricyclic acid to Midazolam which minimizes Isomidazolam formation and provides for non-chromatographic removal of biproducts.

In one embodiment of the present invention is provided a process for the synthesis of a compound of formula I (Midazolam)

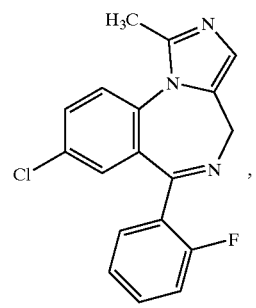

or a pharmaceutically acceptable salt or prodrug thereof, comprising:
(a) forming a first reaction medium comprising from about 1 to about 20 parts by weight of a first solvent system per 1 part by weight of tricyclic acid II,

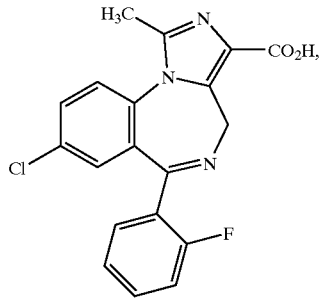

wherein said tricyclic acid exhibits a first critical solution temperature behavior in said first solvent system;
(b) maintaining said first reaction medium at a second temperature of between about 190° C. and about 260° C. such that said compound of formula II decarboxylates to substantially form said compound of formula I; and
(c) isolating said compound of formula I from said first solvent system.

In another embodiment of the present invention is disclosed a method of decarboxylating tricyclic acid to form a Midazolam/Isomidazolam product ratio of about 6:1.

In yet another embodiment of the present invention is disclosed a method of converting the Midazolam/Isomidazolam product ratio from about 6:1 to about 50:1 using thermodynamic, basic workup conditions.

In still yet another embodiment of the present invention is disclosed a method of isolating and purifying Midazolam without using column chromatography.

DETAILED DESCRIPTION OF THE INVENTION

All patents, patent applications, and literature references cited in the specification are hereby incorporated by reference in their entirety. In the case of inconsistencies, the present disclosure, including definitions, will prevail.

Percentages obtained by HPLC analysis are defined by peak area calculations.

As used in the specification and the claims, the following terms have the meanings specified:

The term "alkali metal alkoxide," as used herein, refers to M—OR$^1$, wherein M is a cation selected from the group consisting of lithium, sodium, and potassium, and R¹ is an is an alkyl group, as defined herein.

The term "alkyl," as used herein, refers to a straight or branched chain hydrocarbon radical having from one to twelve carbon atoms. Alkyl groups of this invention include methyl, ethyl, n-propyl, iso-propyl, 2-methylpropyl, n-butyl, 2-butyl, tert-butyl, n-pentyl, 1-methylbutyl, 2,2-dimethylbutyl, 2-methylpentyl, 2,2-dimethylpropyl, n-hexyl, and the like.

The term "base," as used herein, refers to a species capable of abstracting a proton in either a polar or nonpolar solvent. Examples of bases include alkali metal alkoxides as defined herein, alkali metal hydrides such as lithium, sodium, or potassium hydride, and nitrogen-containing bases such as lithium diisopropyl amide (LDA), lithium, sodium, or potassium bis(trimethylsilyl)amide, and the like. It will be obvious to those skilled in the art that individual base and solvent combinations may be preferred for specific reaction conditions depending upon such factors as the solubility of reagents, reactivity of reagents with Isomidazolam or the solvent, and preferred temperature ranges.

The term "first organic extraction solvent," as used herein, refers to a polar solvent, as defined herein.

The term "first solvent system," as used herein, refers to a solvent with a boiling range high enough to promote decarboxylation of tricyclic acid, typically between about 190° C. and about 260° C. First solvent systems of the present invention include. but are not limited to, N,N-dimethylacetamide, phenyl ether, ethylene glycol, propylene glycol, mineral oil, tetrahydronaphthalene, Decalin™ (decahydronaphthalene), and mixtures thereof.

The term "nonpolar solvent" as used herein, refers to a solvent that is relatively inert to proton activity, i.e., not acting as a proton donor. Examples include, but are not limited to, hydrocarbons such as pentane, hexane, heptane, cyclopentane, cyclohexane, and isomers thereof, aromatic solvents such as benzene, toluene, and o-, m-, and p-xylenes 5 halogenated hydrocarbons, such as, methylene chloride, ethylene chloride, chloroform, and the like, heterocyclic compounds, such as, for example, tetrahydrofuran and N-methylpyrrolidinone, and ethers such as diethyl ether and bis(methoxymethyl) ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick, et al., Vol. II, in the Techniques of Chemistry Series, John Wiley & Sons, NY, 1986.

The term "pharmaceutically acceptable prodrugs," as used herein, refers to those prodrugs of Midazolam which are, within the scope of sound medical judgement, suitable for use in contact with the tissues of humans and lower animals without undue toxicity, irritation, allergic response, and the like, commensurate with a reasonable benefit/risk ratio, and effective for their intended use.

The term "polar solvent," as used herein, refers to a solvent that tends to provide protons, such as an alcohol, for example, methanol, ethanol, propanol, iso-propanol, butanol, tert-butanol, or a solvent polarized due to the presence of an electron withdrawing group, such as acetonitrile or tetrahydrofuran, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Method of Purification.* 4th ea., edited by John A. Riddick, et al., Vol. II, in the Techniques of Chemistry Series, John Wiley & Sons, New York, 1986.

The term "prodrug," as used herein, refers to compounds which are rapidly transformed in vivo to Midazolam, for example, by hydrolysis in blood. A thorough discussion is provided in T. Higuchi and V. Stella, Pro-Drugs as Novel Delivery Systems, Vol. 14 of the A.C.S. Symposium Series and in Edward B. Roche, ea., Bioreversible Carriers in Drug Design, American Pharmaceutical Association Press, 1987.

The term "pharmaceutically acceptable salt," as used herein, refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well-known in the art. For example, S. M Berge, et al. describe pharmaceutically acceptable salts in detail in *J. Pharmaceutical Sciences,* 1977, 66:1–19. The salts can be prepared in situ during the final isolation of Midazolam, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations including, but not limited to, ammonium, tetramethylammoniumn, and tetraethylammonium. Preferred pharmaceutically acceptable salts of Midazolam are hydrochloride and maleate.

The term "second organic extraction solvent," as used herein, refers to a nonpolar solvent, as defined herein.

The compounds and processes of the present invention will be better understood in connection with Scheme 1 and Example 1, each of which is intended as an illustration of, and not a limitation upon, the scope of the invention as defined in the appended claims.

Scheme 1

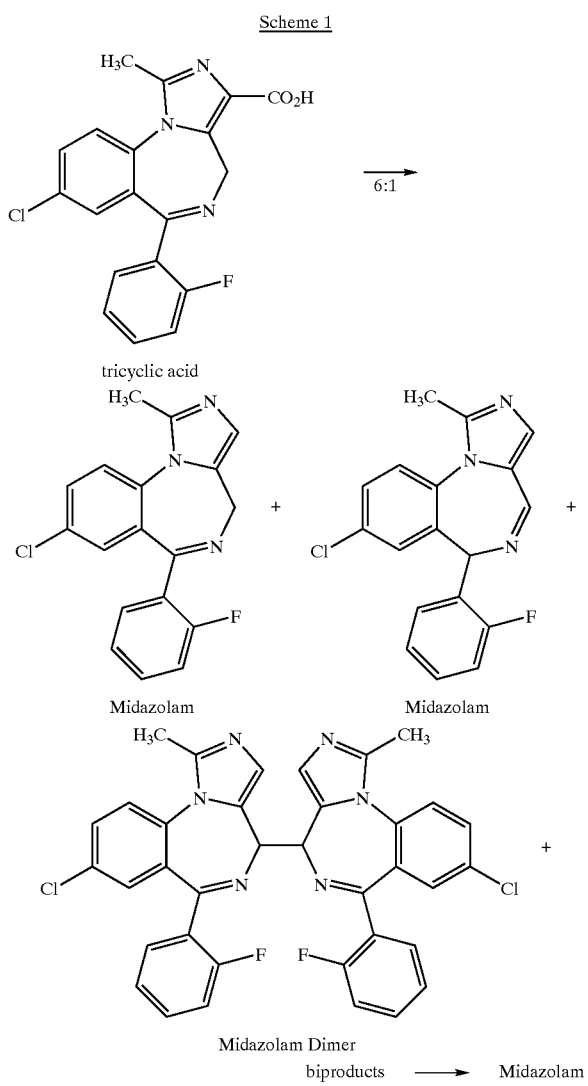

A preferred embodiment is shown as Scheme 1. Tricyclic acid, in a first solvent system such as mineral oil or N,N-dimethylacetamide, was heated to a temperature of between 160° C. and 230° C., until it substantially decarboxylated to form Midazolam, Isomidazolam, and biproducts. In an improvement over preexisting syntheses, adjusting the weight ratio of the first solvent system to tricyclic acid from about 4:1 to about 10:1 increased the Midazolam/Isomidazolam product ratio from about 3:1 to about 6:1. After cooling, the crude first reaction medium was treated with a nonpolar solvent, such as heptane, which was miscible with the first solvent system, but in which the crude Midazolam/Isomidazolam mixture is insoluble. In a preferred embodiment, the reaction mixture is extracted with a polar organic solvent, such as methanol, such that the product mixture substantially dissolved into the methanol to form a first extraction medium. The first solvent system, insoluble in the polar solvent, was separated and discarded. For the preferred thermodynamic, basic workup conditions, treatment of the first extraction medium with a strong base, such as potassium tert-butoxide, to form a second reaction medium and heating the resulting second reaction medium to reflux increased the the Midazolam/Isomidazolam product ratio to about 50:1. After cooling, the methanol insoluble Midazolam dimer which precipitated was removed from the reaction mixture by filtration. The second reaction medium was again heated to reflux, treated with water, and cooled to precipitate Midazolam which was of about 98% purity. Two recrystallizations from ethyl acetate/heptane or isopropyl acetate/heptane provided Midazolam of greater than 99.8% purity as determined by HPLC analysis.

EXAMPLE 1

8-chloro-6-(2-fluorophenyl)-1-methyl-4H-imidazot 1.5-a][1,4benzodiazeline (Midazolam)

A mixture of of 8-chloro-6-(2-fluorophenyl)-1-methyl-4H-imidazo[1,5-a][1,4]benzodia-zepine-3-carboxylic acid (100 g) in mineral oil (1000 g) under nitrogen was heated at 230° C. for 3 hours, cooled, and partitioned between methanol (400 mL) and heptane (400 mL) with stirring. The methanol layer was separated, and the heptane layer was extracted with methanol (150 mL). The methanol extracts were combined, washed with heptane (350 mL), stirred with activitated carbon (20 g) for 2 hours, and filtered through filter aid (40 g) with a methanol rinse (200 mL). The filtrate was concentrated to a volume of 750 mL, transferred to a flask containing potassium tert-butoxide (64 g), stirred at reflux for 3.5 hours and at room temperature for 4 hours, filtered into another flask, concentrated to approximately one-half of its original volume, heated at reflux stirring, treated with water (950 mL), stirred at reflux for minutes, and cooled to room temperature for 4 hours, after which a solid crystallized from solution. The solid was filtered, washed with water (150 mL), dried, and dissolved in acetonitrile (10 mL). This solution was stirred with activated carbon (20 g) for 2 hours then filtered through filter aid (20 g), washed with acetonitrile (200 mL), and concentrated to dryness. The resulting solid was dissolved into ethyl acetate (700 mL), filtered to remove the insolubles, concentrated to 260 mL, and treated with heptane (500 mL) to precipitate the product. The product crystallized for a further 8–18 hours at room temperature and was then filtered, washed with heptane (75 mL) and recrystallized twice from ethyl acetate/heptane to provide 48 g (54.5%) of Midazolam.

mp 162° C. to 164° C. (Lit. 158° C. to 160° C.).

What is claimed is:

1. A process for the synthesis of a compound of formula I

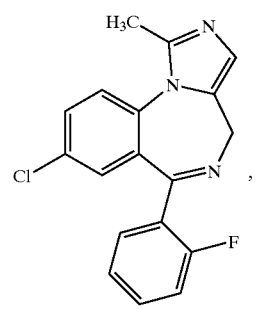

or a pharmaceutically acceptable salt thereof, comprising:
 (a) heating a first reaction medium, at atmospheric pressure, at about 190° C. to about 260° C.,
wherein said first reaction medium comprises from about 1 to about 20 parts by weight of a first solvent per 1 part by weight of tricyclic acid II,

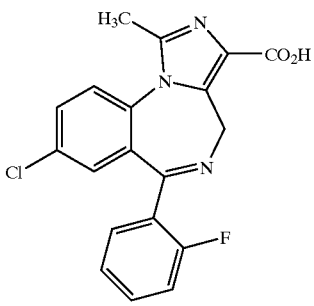

and wherein said first solvent is selected from the group consisting of decahydronaphthalene, ethylene glycol, mineral oil, phenyl ether, propylene glycol, and tetrahydronaphthylene,
to provide the compound of formula I and Isomidazolam in a ratio of about 6:1;

(b) reacting the product of step (a) with a base of formula M—OR$^1$ wherein M is a cation selected from the group consisting of lithium, sodium, and potassium, and R$^1$ is alkyl, in a second reaction medium to provide the compound of formula I and Isomidazolam in a ratio of about 50:1; and (c) isolating the compound of formula I, wherein the foregoing synthesis is conducted without column chromatography.

2. The process according to claim 1, wherein said first solvent is mineral oil.

3. The process according to claim 1, further comprising (d) cooling said first reaction medium;

(e) mixing said first reaction medium and a first extraction medium, wherein said first extraction medium comprises a first extraction solvent either alone or in combination with a second extraction solvent, such that said compound of formula I substantially dissolves in said first extraction solvent to form a second extraction medium, and (f) isolating said second extraction medium.

4. The process according to claim 3, wherein said first extraction medium comprises a first extraction solvent in combination with a second extraction solvent.

5. The process according to claim 4, wherein said first extraction solvent is selected from the group consisting of methanol, ethanol, isopropanol, n-butanol and acetonitrile.

6. The process according to claim 5, wherein said first extraction solvent is methanol.

7. The process according to claim 3, wherein said second extraction solvent is a nonpolar solvent.

8. The process according to claim 7, wherein said second extraction solvent is heptane.

9. The process according to claim 1, wherein R$^1$ is tert-butyl.

10. The process according to claim 1, wherein M is potassium.

11. The process according to claim 3, further comprising (g) mixing said second extraction medium with the base of formula M—OR$^1$ to form said second reaction medium and heating the second reaction medium;

(h) cooling said second reaction medium to precipitate, substantially, Midazolam dimer; and (i) separating said Midazolam dimer from said second reaction medium.

12. The process according to claim 1 further comprising (j) concentrating, at reflux, said second reaction medium to about one-half of its original volume; and (k) mixing with water then cooling said second reaction medium such that said compound of formula I substantially precipitates.

* * * * *

UNITED STATES PATENT AND TRADEMARK OFFICE
CERTIFICATE OF CORRECTION

PATENT NO.    : 6,512,114 B1
DATED         : January 28, 2003
INVENTOR(S)   : Madhup K. Dhaon et al.

It is certified that error appears in the above-identified patent and that said Letters Patent is hereby corrected as shown below:

<u>Column 8,</u>
Line 30, replace the word "claim 1" with the word -- claim 11 --.

Signed and Sealed this

Twelfth Day of August, 2003

JAMES E. ROGAN
*Director of the United States Patent and Trademark Office*